United States Patent [19]

Weston et al.

[11] 4,140,691

[45] Feb. 20, 1979

[54] PROCESS FOR PREPARING 3-[2-(4-BENZAMIDOPIPERID-1-YL)ETHYL-]INDOLE

[75] Inventors: George O. Weston, Havant; Susan E. Murfitt, Petersfield, both of England

[73] Assignee: John Wyeth & Brother, Ltd., Maidenhead, England

[21] Appl. No.: 775,660

[22] Filed: Mar. 8, 1977

[30] Foreign Application Priority Data

Mar. 12, 1976 [GB] United Kingdom ............... 10116/76

[51] Int. Cl.$^2$ .......................................... C07D 401/06
[52] U.S. Cl. .................................... 546/201; 546/273
[58] Field of Search ....................... 260/293.52, 293.61

[56] References Cited

PUBLICATIONS

Ito, I., et al., Tetrahedron, 30, 1027–1031 (1974).
Brown, H., et al., J. Am. Chem. Soc., 77, 6209 (1955).

*Primary Examiner*—Natalie Trousof
*Assistant Examiner*—Richard A. Schwartz
*Attorney, Agent, or Firm*—Arthur E. Wilfond

[57] ABSTRACT

The invention provides a process for preparing indole derivatives in which a compound containing an indole ring linked to an acylamido piperidine ring by a carbonyl alkylene group between the nitrogen of the piperidine and the 3-position of the indole is reduced with alkali-metal borohydride in special solvents so that the carbonyl group is reduced to a $CH_2$ group.

2 Claims, No Drawings

PROCESS FOR PREPARING 3-[2-(4-BENZAMIDOPIPERID-1-YL)ETHYL]INDOLE

The invention relates to a novel process for preparing indole derivatives.

Our U.K. Specification No. 1,218,570 describes inter alia compounds of general formula

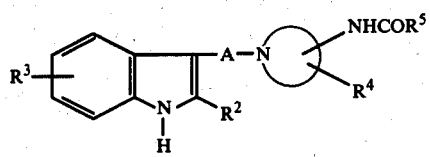

in which formula 

represents a ring system of the general formula

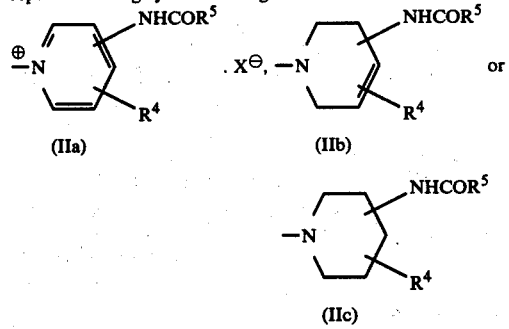

$R^2$ represents hydrogen, lower alkyl or aryl; $R^3$ represents hydrogen, halogen, lower alkoxy, hydroxy or lower alkyl; $R^4$ represents hydrogen, halogen or lower alkyl; $R^5$ represents aryl (including heteroaryl), lower alkoxy, aryloxy, lower aralkyl, lower aralkyloxy or diaryl-lower alkyl; $X^\ominus$ is an anion; A represents an alkylene radical having from 2 to 4 carbon atoms; the terms "lower alkyl" and "lower alkoxy" mean the radical contains 1 to 6 carbon atoms and the term "lower aralkyl" means the radical contains 7 to 10 carbon atoms.

As a modification of that invention we described in our U.K. Specification No. 1 364 314 corresponding compounds where A represents a hydroxyalkylene chain of up to 4 carbon atoms. These compounds may be prepared by selective reduction of corresponding compounds of formula I where A is a mono or diketo alkylene radical. Reduction of the monoketoalkylene compounds may be carried out with an alkali metal borohydride in various solvents.

We have now surprisingly found that treatment of a compound of formula I wherein A represents —CO(CH$_2$)$_n$— and n is 1, 2 or 3 with an alkali-metal borohydride, e.g. sodium borohydride in certain solvents under certain conditions gives a compound of formula I wherein A represents —CH$_2$(CH$_2$)$_n$— instead of the expected compound of formula I wherein A represents CHOH(CH$_2$)$_n$.

The invention is also applicable to corresponding compounds in which $R^5$ is cycloalkyl of 5 to 7 carbon atoms, e.g. cyclohexyl, which compounds are described in our U.K. Specification No. 1 273 563.

Accordingly the present invention provides a process for preparing a compound of formula I, wherein $R^2$, $R^3$, and $R^4$ are as defined in connection with formula I, $R^5$ is as defined in connection with formula I or is cycloalkyl of 5 to 7 carbon atoms, A is lower alkylene of 2 to 4 carbon atoms, and

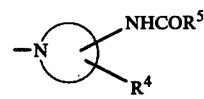

is a ring system of formula IIc, which process comprises treating a compound of formula I wherein A is —CO(CH$_2$)$_n$— wherein n is 1, 2 or 3, and $R^2$, $R^3$, $R^4$ and $R^5$ are as defined above and

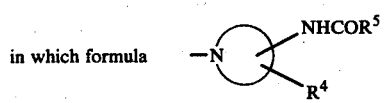

is a ring system of formula IIa, b, or c, with an alkali metal borohydride in a solvent in which the borohydride is stable at a temperature and for a time sufficient to cause complete reduction of the alkylene chain —CO(CH$_2$)$_n$— to CH$_2$(CH$_2$)$_n$.

The preferred solvent is isopropanol. Conveniently the reaction is carried out under reflux conditions.

Preferably the alkali-metal borohydride is sodium borohydride but alternative borohydrides are potassium borohydride and lithium borohydride. Preferably the borohydride is employed in a molar ratio of from 1 to 4 mols borohydride per mol of starting material of formula I.

Examples of groups $R^2$, $R^3$, $R^4$, $R^5$ and $X^\ominus$ are the same as those given in U.K. Patent Specification Nos. 1,218,570 or 1,273,563. $R^2$ can be, for example, hydrogen, methyl, ethyl, n-propyl, isopropyl, n-butyl, isobutyl or substituted or unsubstituted phenyl and is preferably hydrogen or methyl. $R^3$ can be, for example, hydrogen, chlorine, methoxy, ethoxy, hydroxy, methyl, ethyl, n-propyl, isopropyl, n-butyl or isobutyl. Preferably $R^3$ is a hydrogen atom.

Examples of $R^4$ are hydrogen, chlorine, methyl, ethyl, n-propyl, isopropyl, n-butyl or isobutyl, though preferably $R^4$ is a hydrogen atom.

$R^5$ can be, for example, phenyl, substituted phenyl (e.g. phenyl substituted by halogen such as chlorine, by alkoxy, such as methoxy or ethoxy, by alkyl such as methyl or ethyl or by methylenedioxy), heterocyclic radicals (such as indolyl, e.g. 3-indolyl; thienyl, e.g. 2-thienyl; or furyl, e.g. 2-furyl), methoxy, ethoxy, phenoxy, benzyl, benzyloxy and diphenylmethyl.

$X^-$ is preferably a halide ion such as a chloride or bromide.

Preferably $R^2$, $R^3$ and $R^4$ are hydrogen and $R^5$ is a phenyl radical. Also it is preferred that the group

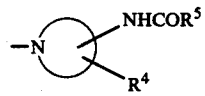

represents a ring system of formula II(c).

If a starting material is used in which

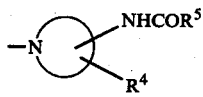

represents a ring system of formula IIa or IIb then under the reducing conditions of the process of this invention the ring system may be reduced to that of formula IIc as described in copending U.S. Application Ser. No. 772,058 filed Feb. 28, 1977 which claims priority from U.K. Application No. 10114/76. This is in contrast to the product of the normal reducing conditions of our U.K. Patent Specification No. 1,364,314 e.g. as used in Example 2, (sodium borohydride in methanol) where reduction to the piperidine ring system (IIc) would not occur. When a ring system of formula IIa or IIb is to be reduced sufficient borohydride will of course have to be employed, one mol being necessary for each double bond in a mol of starting material. However, the new method does not cause reduction of the carbonyl group of an amide link or removal of groups susceptible to hydrogenolysis such as benzyloxycarbonyl.

The products of the process of this invention are of value as pharmaceuticals as described in our U.K. Patent Specification No. 1,218,570 e.g. as hypotensive and anti-hypertensive agents, or U.K. Patent Specification 1,273,563 as hypotensive agents, anti-hypertensive agents or antihistamine agents.

The process of the invention provides a convenient way of synthesising indoramin, a compound first described in U.K. Patent Specification 1,218,570, which is now undergoing clinical evaluation as a hypotensive agent.

The invention is illustrated by the following example.

Example

3-[2-(4-benzamidopiperid-1-yl)ethyl]indole (Indoramin)

A suspension of sodium borohydride (0.5 g.) and 3-[2-(4-benzamidopiperid-1-yl)acetyl]indole (0.3 g.) in isopropanol (5 ml.) was refluxed for 1½ hours. The cooled mixture was diluted with water, acidified to decompose excess sodium borohydride and again made basic with sodium hydroxide. The product was extracted into dichloromethane and washed with water. Evaporation of the solvent gave the crude title compound (0.3 g.); this was purified by solution in dimethylformamide and careful addition of water to give a white crystalline powder m.p. 204°-6° (0.2 g), having infrared spectral characteristics identical with an authentic sample of the title compound.

This example is to be contrasted with Example 2 of the aforementioned U.K. Patent Specification No. 1,364,314 where the same starting material upon reduction with sodium borohydride in refluxing methanol gave 3-[1-hydroxy-2-(4-benzamido-piperid-1-yl)ethyl]indole.

We claim:

1. A process for preparing 3-[2-(4-benzamidopiperid-1-yl)ethyl] indole, wherein 3-[2-(4-benzamidopiperid-1-yl)acetyl] indole is reduced by an alkali metal borohydride in isopropanol to give 3-[2-(4-benzamidopiperid-1-yl)ethyl] indole.

2. A process as claimed in claim 1 wherein the reducing agent is sodium borohydride.

* * * * *